United States Patent [19]

Joseph

[11] Patent Number: 4,604,087
[45] Date of Patent: Aug. 5, 1986

[54] AQUEOUS HUMOR DRAINAGE DEVICE

[76] Inventor: Neil H. Joseph, 54 Hereford Road, London W.2., England

[21] Appl. No.: 747,409

[22] Filed: Jun. 21, 1985

[30] Foreign Application Priority Data

Feb. 26, 1985 [GB] United Kingdom ............... 8504905

[51] Int. Cl.⁴ ............................................. A61M 27/00
[52] U.S. Cl. ........................................ 604/9; 604/294
[58] Field of Search ................................. 604/8–10, 604/174, 294

[56] References Cited

U.S. PATENT DOCUMENTS

| 3,159,161 | 12/1964 | Ness | 604/8 |
|---|---|---|---|
| 3,788,327 | 1/1974 | Donowitz et al. | 604/9 |
| 4,037,604 | 7/1977 | Newkirk | 604/9 |
| 4,402,681 | 9/1983 | Haas et al. | 604/9 |
| 4,457,757 | 7/1984 | Molteno | 604/294 |
| 4,521,210 | 6/1985 | Wong | 604/8 |

FOREIGN PATENT DOCUMENTS 2101891 1/1983 United Kingdom .

OTHER PUBLICATIONS

Chandler, "Long-Term Results in Glaucoma Therapy", American Journal of Ophthalmology, vol. 49, 1960, pp. 221–246.
Quigley and Maumenee, "Long-Term Follow-Up of Treated Open-Angle Glaucoma", American Journal of Ophthamology, vol. 87, 1979, pp. 519–525.
Abedin, Simmons and Grant, "Progressive Low-Tension Glaucoma", American Academy of Ophthalmology, vol. 89, 1982, pp. 1–6.
Molteno, "New Implant for Drainage in Glaucoma--Clinical Trial", Brit. J. Ophthal., vol. 53, 1969, pp. 606–615.
Molteno, "A New Implant for Glaucoma-Effect of Removing Implants", Brit. J. Ophthalmology, vol. 55, 1971, pp. 28–37.
Molteno, "Children with Advanced Glaucoma--Treated by Draining Implants", So. African Archive of Ophthalmology, vol. 1, No. 1, 1973, pp. 55–62.
Molteno, Straughan & Ancher, "Long Tube Implants in the Management of Glaucoma", So. African Medical Journal, vol. 50, 1976, pp. 1062–1066.
Bartholomew, "Glaucoma Implants–Their Use in Difficult Cases of Glaucoma", Transactions Ophthal. Soc. U.K., vol. 98, 1978, pp. 482–485.
Molteno, "The Optimal Design for Drainage Implants in Glaucoma", Transactions of the Ophthalmological Society of New Zealand, vol. 33, 1981, pp. 39–41.
Ancker and Molteno, "Molteno Drainage Implant for Neovascular Glaucoma", Transactions of Ophthal. Soc. of U.K., vol. 102, 1982, pp. 122–124.
Brown and Cairns, "Experience with the Molteno Long Tube Implant", Transactions of Ophthal. Soc. of U.K., vol. 103, 1983, pp. 297–312.
Molteno, "Uveitis with Glaucoma Treated by Implants", So. African Archive of Ophthalmology, vol. 1, No. 2, 1973, pp. 125–130.
Ancker and Molteno, "Management of Neovascular Glaucoma with the Molteno Implant", ACTA. 24th Int. Congress of Ophthal., 1982, pp. 627–629.
Cairns, "The Molteno Long-Tube Implant", Transactions of Ophthal. Soc. of U.K., vol 103, 1983, pp. 39–41.
Molteno, Ancker and Van Bilfon, "Surgical Technique for Advanced Juvenile Glaucoma:, Archives of Ophthal., vol. 102, 1984, pp. 51–57.

(List continued on next page.)

Primary Examiner—Dalton L. Truluck
Attorney, Agent, or Firm—Russell & Tucker

[57] ABSTRACT

A device for draining aqueous humor from an eye comprises a drainage tube and a drainage body. The drainage tube drains aqueous humor from the anterior chamber of the eye, and the drainage body distributes drained aqueous humor over a relatively large area. The drainage tube is firmly fixed to the drainage body, and opens directly on to a surface of the drainage body. The drainage body is constituted by a silicone rubber band having a width of at least 5 mm and a length which is sufficient for the band to pass around, and to be sutured to, the sclera of the eye in an equatorial position. The device is provided with a pressure gradient limiting valve having a predetermined opening pressure.

14 Claims, 11 Drawing Figures

OTHER PUBLICATIONS

Molteno, Van Biljon and Ancker, "Two-Stage Insertion of Glaucoma Drainage Implant", Transactions of Ophthalmology Society of New Zealand, vol. 31, 1979, pp. 17-26.

Schocket, Lakhampal and Richards, "Anterior Chamber Tube Shunt to an Encircling Band in the Treatment of Neovascular Glaucoma", Ophthalmology, vol. 89, 1982, pp. 1188-1194.

Sarkies and Hitchings, "Silicone Tube and Gutter in Advanced Glaucoma", Trans. of Ophthal. Soc. of U.K., vol. 104, 1985, pp. 133-136.

Krupin, Steven Podos, Becker & Newkirk, "Valve Implants in Filtering Surgery:, American Journal of Ophthalmology, vol. 81, 1976, pp. 232-235.

Krupin, Kaufman, Mandell, Ritch, Asseff, Podos and Becker, "Filtering Valve Implant Surgery for Eyes with Neovascular Glaucoma", American Journal of Ophthalmology, vol. 89, 1980, pp. 338-343.

Krupin, Kaufman, Mandell, Terry Ritch, Podos and Becker, "Long-Term Results of Valve Implants in Filtering Surgery for Eyes with Neovascular Glaucoma:, American Journal of Ophthalmology, vol. 95, 1983, pp. 775-782.

Sutton, Popp & Records, "Krupin-Denver Valve and Neovascular Glaucoma", Trans. of Ophthalmology Society of U.K. vol. 102, 1982, pp. 119-121.

Folber, Hargett, Weaver and McLean, "Filtering Valve Implant for Neovascular Glaucoma in Proliferative Dabetic Retinopathy", Ophthalmology, vol. 89, 1982, pp. 286-289.

Vision Research; A National Plan 1983-87, vol. 2/Part 4, National Institute of Health; Publication No. 83-2472, p. 1.

W. Morton Grant, et al., "Why Do Some People Go Blind from Glaucoma?" Ophthalmology vol. 89, pp. 991-998, 1982.

Saiichi Mishima, et al., "Current Status of Glaucoma Surgery"; XXI V International Congress of Ophthalmology, San Francisco; pp. 599-605, 1982.

Saiichi Mishima, et al., "Surgical Treatment of Open-Angle Glaucoma"; Australian and New Zealand Journal of Ophthalmology, vol. 19, pp. 211 to 223, 1985.

Werner Cadera, et al., "Surgery in Childhood Glaucoma", Ophthalmic Surgery, vol. 15, pp. 319 to 322, 1984.

Ralph Z. Levene, "Glaucoma Filtering Surgery: Factors that Determine Pressure Control", Ophthalmic Surgery, vol. 15, pp. 475 to 483, 1984.

Kathleen A. Lamping, et al.; "Long-Term Evaluation of Initial Filtration Surgery", Ophthalmology, vol. 93, pp. 91 to 102; 1986.

Don Minckler; ARVO Abstracts 12-6:45, p. 126, 1985.

A. Edward Maumenee; "External Filtering Operations for Glaucoma: The Mechanism of Function and Failure", Transation American Ophthalmology Society, vol. 58, pp. 319-328, 1960.

Miguel F. Rejofo, "Current Status of Biomaterials in Ophthalmology", Survey of Ophthalmology, vol. 26, pp. 257-265, 1982.

Sherwood, et al; "Complications of Silicone Tube Implant38 , submitted to American Journal of Ophthalmology, Feb., 1986.

Stanley S. Schocket, et al; "Anterior Chamber Tube Shunt to an Encircling Band in the Treatment of Neovascular Glaucoma and Other Refractory Glaucomas", Ophthalmology, vol. 92, pp. 553-562, 1985.

Theodore Krupin, "Surgical Treatment of Glaucoma with the Krupin-Denver Valve"; (given to Dr. Joseph by Dr. Krupin at Scheie Eye Institute on Wed., 7 Aug., 1985 during a two hour conversation during which Dr. Joseph asked Dr. Krupin to xerox a copy).

F. Peter Kohler, et al; "A Mechanical Ureteral Valve", Surgery Gynecology & Obstetrics; 109:703-708; 1959.

Thomas C. White, European Patent Application No. 0 102 747 A1, published 14.03.84 Bulletin, 84/11.

M. H. Miller, et al; "Drainage Implant Surgery in the Treatment of Glaucoma:.A Review"; Seminars in Ophthalmology, vol. 1, 1986.

Svein Ore, et al; "Preparation of Surgical Implants from Silicone Rubber by Means of a Postforming Technique"; Surgery vol. 52, No. 2, pp. 385-390; 1962.

AQUEOUS HUMOR DRAINAGE DEVICE

BACKGROUND OF THE INVENTION

This invention relates to a device for draining aqueous humor from a human eye for the relief of glaucoma.

Glaucoma is an eye condition in which, from various causes, the intra-ocular pressure (that is to say the pressure of the aqueous humor in the eye) rises, tending to make the eyeball hard and, in high-tension glaucoma, adversely affecting vision and even causing partial or total loss of sight.

A known method of treating glaucoma is filtration surgery, either with or without implanted drainage devices. In a filtering operation which does not involve an implanted drainage device, an opening is cut into the anterior chamber of the eye (the opening being formed under a flap of conjunctiva) to drain aqueous humor to a bleb which forms over the sclera. The aqueous humor in the bleb seeps away over a period to small blood vessels and lymphatic vessels. Filtering operations of this type are reasonably successful. Unfortunately, however, about 20% fail over a period of time following the operation, and about 30% lead to cataract formation. The main reason for these problems is a result of poor control of the filtering opening, and subsequent reduction in the drainage flow of aqueous humor. The resulting ocular hypotony may lead to cataract formation, and does lead to the apposition of tissues and scarring at the site of the sclerostomy, and this gives rise to failure of the operation.

Although various attempts have been made to overcome these problems by the use of implant devices, none of these has proved entirely successful. Implant devices utilise drainage tubes to maintain the integrity of the openings formed in diseased eyes for the flow of aqueous humor. Typically, the drainage tube of such a device leads to a drainage body which is sutured to the sclera. The purpose of the drainage body is to increase the drainage area, and hence to ensure that aqueous humor drains away at a sufficiently high rate. After such a device is surgically implanted, scar tissue forms around the drainage body, the aqueous humor filtering through this scar tissue to the blood and lymphatic vessels. This scar tissue helps to immobilise the device. However, if the scar is too thick, it resists filtration of aqueous humor to the surrounding blood and lymphatic vessels. In this connection, a thick scar is analagous to multiple layers of filter paper, in that both require a larger surface area (than a thin scar or a single layer of filter paper) to ensure the same rate of filtration. Thus, when thick scar tissue forms with this type of device, failure follows owing to inadequate surface area of the drainage body. In a normal eye, the pressure of aqueous humor in the anterior chamber is about 14 to 16 mm of mercury. A device may be said to have failed, when the pressure in the anterior chamber is greater than 18 mm of mercury. A medically accepted test for a successful drainage device is one that ensures that the intra-ocular pressure remains below 18 mm of mercury for at least six months following implantation.

A typical known implant device (see British Patent Specification No. 2 101 891) utilises a thin silicone rubber drainage tube which leads to one or more ridged circular plates. The circular plate(s) form a drainage body, which is sutured to the sclera of the eye. This type of device has a high failure rate, because the surface area of the drainage body is inadequate to ensure sufficient drainage of aqueous humor.

The object of the invention is to provide an aqueous humor drainage device which does not suffer from the disadvantages of known devices, and which can ensure that the intra-ocular pressure remains below 18 mm of mercury for at least six months following implantation for the majority of patients.

SUMMARY OF THE INVENTION

The present invention provides a device for draining aqueous humor from an eye, the device comprising a drainage tube for draining aqueous humor from the anterior chamber of an eye, and a drainage body for distributing drained aqueous humor over a relatively large area, the drainage tube being firmly fixed to the drainage body and opening directly on to a surface of the drainage body, and the drainage body being constituted by a band having a width of at least 5 mm and a length which is sufficient for the band to pass around, and to be sutured to, the sclera of the eye in an equatorial position, wherein the device is provided with a pressure gradient limiting valve having a predetermined opening pressure.

The use of a band of such a width and length ensures that there is a sufficiently large filtration area to ensure that the intra-ocular pressure remains below 20 mm of mercury for at least six months following implantation for the majority of patients. Moreover, the fixing of the tube to the band prevents scar tissue forming around the opening (which otherwise could block the flow of aqueous humor to said surface of the band). The provision of the pressure gradient limiting valve ensures that the initial flow of aqueous humor away from the anterior chamber is restricted to a level which permits adequate circulation of aqueous humor over the lens of the eye.

Advantageously, the pressure gradient limiting valve is positioned at that end of the tube which is fixed to the band, the valve constituting the opening through which aqueous humor flows directly to said surface of the band. Preferably, the pressure gradient limiting valve is constituted by at least one slit formed in the wall of the tube.

In a preferred embodiment, the tube is preformed to follow the arc of a circle, the diameter of which is such that, in use, the free end of the tube is positioned within the anterior chamber of the eye closer to the iris than the cornea. Preforming the tube in this way ensures that the free end of the tube can easily be positioned in the anterior chamber well clear of the cornea, and this is advantageous as the tube could damage the cornea if it touches the cornea. For most eyes, the diameter of said circle is preferably about 30 mm.

Preferably, the tube and the band are made of physiologically inert material such as medical grade silicone rubber or a hydrogel (such as hydroxyethylmethacrylate).

For most eyes, the band preferably has a width lying in the range of from 9 to 12 mm, and the pressure gradient limiting valve has an opening pressure of from 4 to 20 mm of mercury. Conveniently, the tube is fused or glued to the band.

In a preferred embodiment, the tube extends beyond the band, the end of the extended portion being closed. In this case, the device may further comprise an additional drainage body and an additional tube, one end of the additional tube being connectible to the extension of the first-mentioned tube, after said closed end thereof has been opened, the other end of the additional tube being fixed to the additional drainage body and opening directly on to a surface of the additional drainage body. Advantageously, an additional pressure gradient limiting valve is provided in the additional tube. The additional drainage body can be implanted (preferably under the scalp) some time after the initial operation, if the intra-ocular pressure rises too high owing to inadequate filtration resulting from excessive scar formation. This can be accomplished by simple extra-ocular surgery. If necessary, further drainage area can subsequently be provided by connecting a further drainage body to the additional drainage body to make a physically continuous body.

BRIEF DESCRIPTION OF THE DRAWINGS

Two forms of aqueous humor drainage device, each of which is constructed in accordance with the invention, will now be described in detail, by way of example, with reference to the accompanying drawings, in which.

DESCRIPTION OF PREFERRED EMBODIMENTS

Figure 1:
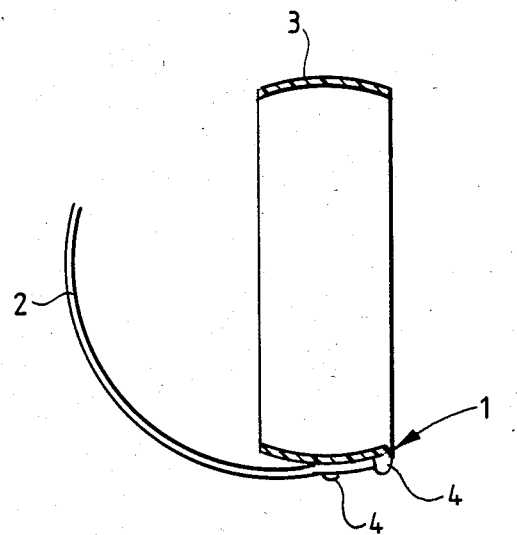
FIG. 1 is a schematic cross-section through the first form of device.

Referring to the drawings, FIG. 1 shows an aqueous humor drainage device 1 having a drainage tube 2 and a drainage body 3. The tube 2 is made of medical grade silicone rubber, and has a length of 24 mm, a wall thickness of 0.175 mm and a bore of 0.3 mm. The drainage body 3 is a band of medical grade silicone rubber having a width of 9 mm and a thickness of 0.75 mm. The tube 2 is fixed to the band 3 by fusing or gluing (as indicated by the reference numerals 4). In practice, the raised portions of the fusing or glue are removed to leave a flush surface. The tube 2 is formed with one or more slits 5 (see FIGS. 3a to 3d) in that portion which is fixed to the band 3. The slit(s) in the tube 2 form a pressure gradient limiting valve. The tube 2 is preformed to follow the arc of a circle of diameter 30 mm.

Figure 2:
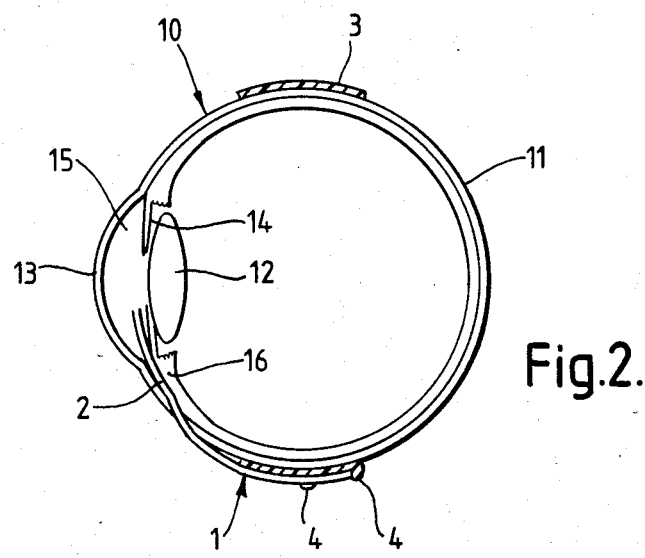
FIG. 2 is a schematic representation showing the device of FIG. 1 implanted in an eye.

FIG. 2 shows the device 1 implanted in an eye 10. The eye 10 is an average-sized diseased eye, that is to say one having a diameter of about 25 mm. The curvature of the tube 2 is chosen to match this eye diameter, as will be described below. Similarly, the circumference of the band 3 is chosen so that it is just the right length to be sutured to the sclera 11 of the eye 10 at an equatorial position. In use, the two ends of the band 3 are sutured together after the band has been positioned, and, if necessary, trimmed (that is to say, if it is too long for the eye). FIG. 2 shows the lens 12, the cornea 13, the iris 14 and the anterior chamber 15 of the eye 10. This figure also shows the free end of the tube 2 entering the anterior chamber 15 through an opening in the cyclodialysis tract 16, the opening being formed surgically. FIG. 2 also shows that the preformed curvature of the tube 2 is such that the free end of the tube lies about one third of the distance between the iris 14 and the cornea 13. Moreover, this preformed curvature ensures automatic positioning of the free end of the tube 2 in this manner. This is extremely important, as it is essential that the free end of the tube 2 does not touch the corneal endothelium (the cell area of the back of the cornea 13). If this did happen, the cornea 13 would become opaque, and this is clearly undesirable. By curving the tube 2 in this manner, the free end of the tube 2 is automatically positioned well behind the corneal endothelium, and so this undesirable prospect is prevented without the surgeon having to take special precautions. Moreover, the curvature chosen is suitable for automatic positioning well clear of the corneal endothelium in a wide variety of sizes and shapes of human eyes. Obviously, for eyes which are much smaller or larger than the "normal" eye, the curvature of the tube 2 will appropriately be smaller or larger than of 30 mm diameter.

Figure 3A:
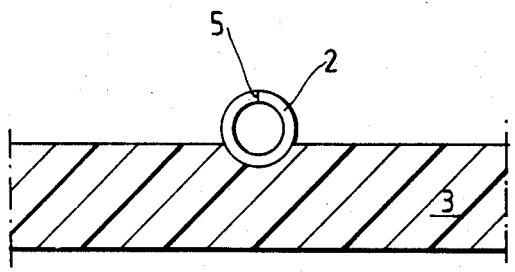
FIGS. 3a to 3d are enlarged schematic views showing alternative valve arrangements that can be incorporated in the device of FIG. 1.
Figure 3B:
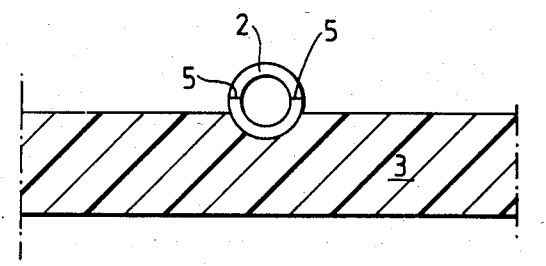
Figure 3C:
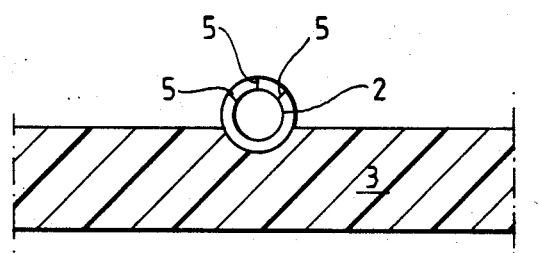
Figure 3D:
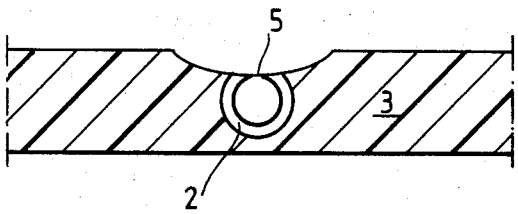

FIG. 3a shows a first form of pressure gradient limiting valve, which is constituted by a single slit 5 in the "top" of the tube 2, the slit 5 having a length of 3 mm. FIGS. 3b and 3c show valve modifications having two and three slits 5 respectively. FIG. 3d shows a further modification, in which the tube 2 is fixed (fused) within the body of the band 3, and the slit 5 is formed in the "top" surface of the tube, this top surface being positioned within a concave depression in the band. Depending upon the mechanical properties of the tube wall at the valve site, one or more slits 5 will be required to achieve a desired opening pressure of from 4 to 20 mm of mercury.

The pressure gradient limiting valve is used to control the drainage rate. Thus, the high intra-ocular pressure which exists immediately after entering the eye tends to drain aqueous humor too quickly. This can lead to large choroidal detachments forming, which in turn are associated with a tendency to damage the lens of the eye. The use of the pressure gradient limiting valve prevents this happening, provided the patient does not adversely affect the eye.

The drainage device 1 described above does not suffer from the disadvantages of prior art devices. In particular, the following points should be noted:

(a) The surface area of the band 3 is sufficiently large to ensure adequate filtration. The large surface area of the band 3 ensures that there is an adequate flow of aqueous humor at a physiological pressure gradient, that is to say without an excessively high (greater than 18 mm mercury) intra-ocular pressure, even if there is a thick growth of scar tissue. In this connection, it should be appreciated that the inevitable scar formation is (provided it is not excessively thick) advantageous. This is because the scar tissue slows down (filters) the flow rate of aqueous humor to a rate commensurate with that which can be secreted by the eye and taken up by the blood and lymphatic vessels at a physiological pressure gradient.

(b) The tube 2 is firmly fixed to the band 3, so there is no possibility of scar tissue forming around a loose end thereof and blocking the flow of aqueous humor.

(c) The pressure gradient limiting valve not only prevents initial excessive loss of aqueous humor from the anterior chamber 15, but it is also positioned on a drainage body (the band 3) of a large surface area. Consequently, there is no danger of the valve being blocked by scar tissue, and aqueous humor can flow continuously and directly onto the band, from where it can be filtered through scar tissue to the blood and lymphatic vessels.

It will be apparent that the drainage device 1 described above could be modified in a number of ways. For example, the width of the band 3 may lie within the range of from about 5 mm to 15 mm for a "normal" eye, though the preferred range (for the normal eye) is 9 to 12 mm. In this connection, it should be noted that band widths of between 5 and 9 mm would probably only be satisfactory for elderly patients, whose scarring tendency is less than that of younger people. If band widths greater than about 15 mm are used, there may be problems with the rotation of the eyeball within its orbit, and this could lead to double vision. Accordingly, if the band 3 is placed equatorially and symmetrically, a width of 15 mm should not be exceeded. However, if the band is positioned slightly asymmetrically, a band width of up to about 18 mm for an average eye may be possible. Moreover, the tube 2 and the band 3 need not be made of silicone rubber (though this is currently much the preferred material). These members could, for example, be made of a hydrogel such as hydroxyethylmethacrylate.

It would also be possible to use a preformed angled tube instead of the curved tube. For example, the tube could be angled in and then out so as to follow the shown angled route into the anterior chamber of the eye through the cyclodialysis tract. Although such an angled tube could be used in some circumstances, the curved tube is preferable as inserting a curved tube gives rise to considerably less surgical difficulties. It would also be possible, in some circumstances, to use a straight tube.

Another possible modification would be to form the pressure gradient limiting valve in other ways. For example, if the tube has a wall thickness much less than that mentioned above (0.175 mm), it would be preferable to join the tube to the band, to punch a hole in the band at the junction, to cover both sides of the punched hole with thin membranes, and to form the valve in one of the membranes by making one or more slits therein. The thin membranes could be made of the same material (preferably silicone rubber) as the tube and the band.

As an alternative to fixing or bonding the tube to the band, it would also be possible to fix the tube firmly to the band by a friction fit sleeve made of silicone rubber, so that the tube could not separate from the band (which could lead to blockage by scar tissue).

Figure 4:
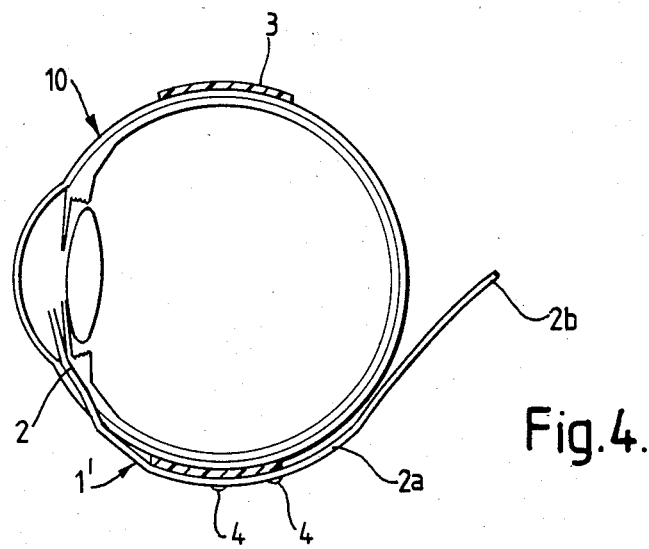
FIG. 4 is a view similar to that of FIG. 2, showing the second form of device implanted in an eye.
Figure 5:
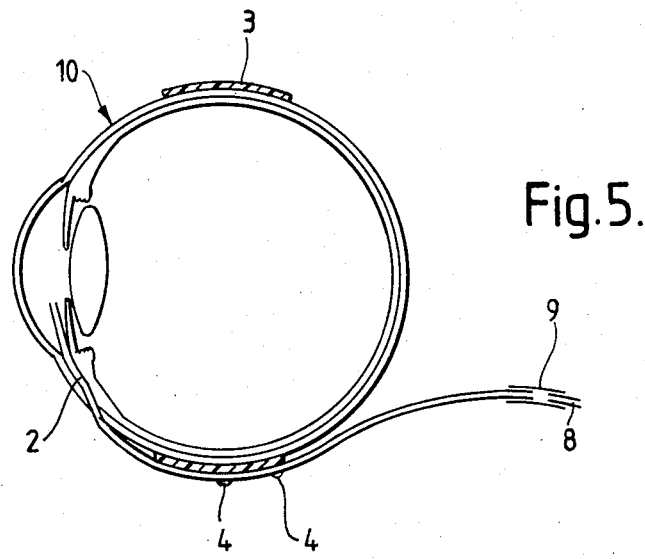
FIG. 5 is a view similar to that of FIG. 4, showing a modified form of device having facilities for adding an additional drainage body.
Figure 6:
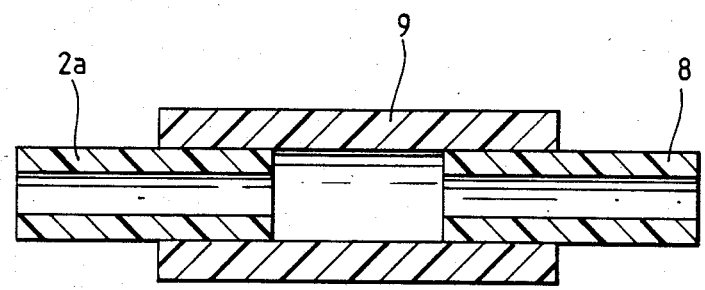
FIG. 6 is an enlarged cross-sectional view of an arrangement for connecting an additional drainage body.
Figure 7:
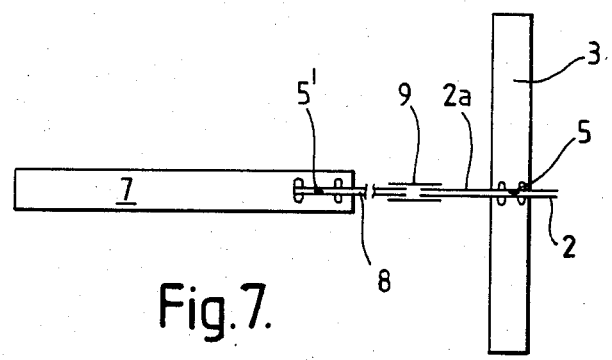
FIG. 7 is a plan view of the second form of device together with an additional drainage body.
Figure 8:
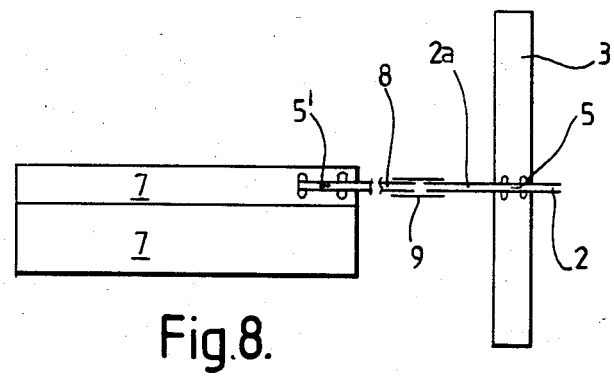
FIG. 8 is a view similar to that of FIG. 7, and shows the addition of a further drainage body.

Although it is envisaged that the device 1 described above will be successful in the vast majority of cases (that is to say will ensure that the intra-ocular pressure will be kept below 18 mm of mercury for at least six months), there will inevitably be problems in some cases. In order to deal with such problems, as they arise, without having to make further incisions into the eye, the modified form of device 1' shown in FIGS. 4 to 8 could be used. This device 1' is similar to the device 1, in that it has a tube 2 and a band 3. The device 1' is shown implanted in an eye 10. However, the tube 2 has an extension 2a (see FIG. 4) which projects beyond that portion thereof which is fixed to the band 3. The end of the extension 2a is normally blocked by a plug 2b.

Should the intra-ocular pressure in the eye 10 rise above 18 mm of mercury (owing to a larger build up of scar tissue round the band 3, and a subsequent reduction in the rate of filtration), an additional drainage body 7 (see FIG. 7) can be implanted to increase the surface area available for drainage. This drainage body 7 is a strip of medical grade silicone rubber, and it is connected to the tube extension 2a (after removal of the plug 2b) by a silicone rubber tube 8 and a connector 9 (see FIG. 6). This connection is maintained by suturing and by a silicone medical adhesive. The drainage body 7 is inserted in an extra-orbital location, preferably under the scalp of the patient. The tube 8 is provided with a pressure gradient limiting valve 5', this valve being similar to the valve provided in the tube 2—being constituted by one or more slits in the tube 8. The opening pressure of the valve 5' can be chosen to be the same as the valve 5, or it can be greater or less than this valve, the choice being dependent upon the patient concerned. The provision of the additional filtering area thus involves a fairly simple surgical operation, which requires no further surgery in the eye itself.

In the unlikely event of the intra-ocular pressure again rising too high, the filtration area can be further increased by simply adding a further drainage body 7' (see FIG. 8), this further body merely being connected to the drainage body 7 by suturing and by silicone medical adhesive. Here again, this is a simple surgical operation, and involves no further surgery on the eye itself.

In some circumstances, the surface area of the band may prove to be too large, and the rate of filtration may be so large that the intra-ocular pressure approaches zero. In such a case, it would be relatively easy to reduce the surface area of the band by removing a portion thereof.

I claim:

1. A device of one piece construction for draining aqueous humor from an eye composed entirely of supple, biologically inert material, the device comprising a drainage body for distributing drained aqueous humor over a relatively large area comprising a band having a width of at least 5 mm, and a length sufficient for the band to pass substantially around, and be sutured to, the sclera of said eye in an equatorial position; a drainage tube integrally and firmly fixed to the drainage body and of sufficient length that an end thereof may be safely disposed within the anterior chamber of said eye; and a pressure gradient limiting slit valve means having a predetermined opening pressure disposed directly proximate to the area of fixation of the drainage tube to the drainage body establishing a direct route of aqueous humor flow between the interior of the drainage tube and a surface of the drainage body, whereby excessive intraocular pressure may be relieved by the controlled drainage of aqueous humor from the anterior chamber of said eye.

2. A device according to claim 1, wherein the pressure gradient limiting valve comprises at least one slit formed in the wall of the tube.

3. A device according to claim 1, wherein the pressure gradient limiting valve comprises a slit formed in the wall of the tube, the slit being generally parallel to, and closely spaced from, said upper surface of said drainage body.

4. A device according to claim 1, wherein the pressure gradient limiting valve's maximum opening exceeds the cross sectional area of the lumen of the drainage tube.

5. A device according to claim 1, wherein the tube is preformed to follow the arc of a circle, the diameter of which is such that the free end of the tube can be positioned within the anterior chamber of the eye closer to the iris than the cornea.

6. A device according to claim 5, wherein the diameter of said circle is about 30 mm.

7. A device according to claim 1, wherein the tube and the band are made of medical grade silicone rubber.

8. A device according to claim 1, wherein the tube and the band are made of a hydrogel such as hydroxyethylmethacrylate.

9. A device according to claim 1, wherein the band has a width lying in the range from 9 to 12 mm.

10. A device according to claim 1, wherein the pressure gradient limiting valve has an opening pressure of from 4 to 20 mm of mercury.

11. A device according to claim 1, wherein the tube is fused or glued to the band.

12. A device according to claim 1, wherein the tube extends beyond the band, the end of the extended portion being closed.

13. A device according to claim 2, further comprising an additional drainage body and an additional tube, one end of the additional tube being connectible to the extension of the first-mentioned tube, after said closed end thereof has been opened, the other end of the additional tube being fixed to the additional drainage body and opening directly on to a surface of the additional drainage body.

14. A device according to claim 13, wherein an additional pressure gradient limiting valve is provided in the additional tube.

* * * * *